US008029562B2

(12) United States Patent
Kitching et al.

(10) Patent No.: US 8,029,562 B2
(45) Date of Patent: Oct. 4, 2011

(54) WETTABLE EPTFE MEDICAL DEVICES

(75) Inventors: Kathryn J. Kitching, Broadgreen (GB); Catherine E. Taylor, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/946,585

(22) Filed: Nov. 15, 2010

(65) Prior Publication Data

US 2011/0060402 A1 Mar. 10, 2011

Related U.S. Application Data

(62) Division of application No. 11/742,433, filed on Apr. 30, 2007, now Pat. No. 7,923,053.

(60) Provisional application No. 60/795,668, filed on Apr. 28, 2006.

(51) Int. Cl.
*A61F 2/06* (2006.01)
(52) U.S. Cl. ......... 623/1.43; 204/164; 606/41; 604/265; 604/230; 623/1.1; 623/1.15; 623/1.42
(58) Field of Classification Search .................. 204/164; 606/41; 604/265, 230; 623/1.43
See application file for complete search history.

(56) References Cited

U.S. PATENT DOCUMENTS

| | | | |
|---|---|---|---|
| 4,193,138 A | | 3/1980 | Okita |
| 4,767,414 A | * | 8/1988 | Williams et al. ............. 604/230 |
| 4,946,903 A | | 8/1990 | Gardella et al. |
| 5,531,715 A | * | 7/1996 | Engelson et al. ............. 604/265 |
| 6,582,429 B2 | * | 6/2003 | Krishnan et al. ............. 606/41 |
| 6,585,765 B1 | | 7/2003 | Hossainy et al. |
| 7,923,053 B2 | | 4/2011 | Kitchling et al. |
| 2001/0045351 A1 | * | 11/2001 | Koh et al. ..................... 204/164 |
| 2003/0180488 A1 | | 9/2003 | Lim et al. |

FOREIGN PATENT DOCUMENTS

EP 201915 11/1986

OTHER PUBLICATIONS

Kitching, K.J., et al., "Modification of Microporous ePTFE Materials to Enhance Wettability", 24th Annual S&T Conference, Abstract, 2005.
Kitching, K.J., et al., "Modification of Microporous ePTFE Materials to Enhance Wettability", 24th Annual S&T Conference, Poster, 2005.
Zhang, Q., et al., "Biocompatibility evaluation of ePTFE membrane modified with PEG in atmospheric pressure glow discharge", JJ Biomed. Mater. Res., vol. 60, pp. 502-509, 2002.
International Searching Authority Report, Apr. 2, 2008.
Kitching, et al., Modification of Microporous ePTFE Materials to Enhance Wettability, 24th Annual S&T Conference, Poster, 2005.
Kitching, et al., Modification of Microporous ePTFE Materials to enhance Wettability, 24th annual S&T Conference, Abstract, 2005.
Zhang, et al., Biocompatibility Evaluation of ePTFE Membrance Modified with PEG in Atmospheric Pressure Glow Discharge, JJ. Biomde. Mater. Res., vol. 60:pp. 502-509, 2002.

* cited by examiner

*Primary Examiner* — Dah-Wei Yuan
*Assistant Examiner* — Andrew Bowman

(57) ABSTRACT

Methods are provided for surface modifying a hydrophobic polymer substrate to increase wettability comprising the steps of pre-treating the hydrophobic polymer substrate with a radio frequency (RF)-generated first plasma and a RF-generated second plasma wherein the first plasma and the second plasma are applied sequentially, coating the hydrophobic polymer substrate with a hydrophilic coating; and polymerizing the hydrophilic coating on the hydrophobic polymer substrate by exposure to a RF-generated third plasma.

9 Claims, 5 Drawing Sheets

… … …

WETTABLE EPTFE MEDICAL DEVICES

CROSS REFERENCE TO RELATED APPLICATIONS

This is a divisional application and claims priority to U.S. application Ser. No. 11/742,433 filed Apr. 30, 2007 which claims priority to U.S. Provisional Application No. 60/795,668 filed Apr. 28, 2006, the entire contents of which is incorporated by reference herein.

FIELD OF THE INVENTION

The present invention relates to surface modification of expanded polytetrafluoroethylene substrates to enhance hydrophilicity and, therefore, wettability.

BACKGROUND OF THE INVENTION

Implantable medical devices have become increasingly more common over the last 50 years and have found applications in nearly every branch of medicine. Examples include joint replacements, vascular grafts, heart valves, ocular lenses, pacemakers, vascular stents, urethral stents, and many others. However, regardless of the application, implantable medical devices must be biocompatible, that is, they must be fabricated from materials that will not elicit an adverse biological response such as, but not limited to, inflammation, thrombogenesis or necrosis. Thus, early medical devices were generally fabricated from inert materials such as precious metals and ceramics. More recently, stainless steel and other metal alloys have replaced precious metals and polymers are being substituted for ceramics.

Polytetrafluoroetheylene (PTFE) is a polymer comprised of carbon chains saturated with fluorine. The use of PTFE in medical applications began in the construction of artificial heart valves. Expanded PTFE is porous, biostable, and implantable medical devices made from it do not degrade within the body.

Expanded polytetrafluoroethylene materials are now widely used in a variety of medical devices; for example, vascular grafts, ablation catheters, etc.

Expanded polytetraflouroethylene offers many advantageous physical properties relating to medical devices. Along with a low coefficient of friction, ePTFE is biocompatible, chemically resistant, linearly strong, UV resistant, waterproof, flexible, etc. However, ePTFE is extremely hydrophobic and not easily wettable. Medical devices made of ePTFE are non-wetting when introduced into an aqueous environment, limiting their use in certain applications.

Therefore, methods to decrease hydrophobicity, and therefore improve wettability, of ePTFE medical devices are needed to optimize these devices.

SUMMARY OF THE INVENTION

The present invention provides methods to render hydrophobic polymers wettable. In one embodiment of the present invention, expanded polytetrafluoroethylene (ePTFE) is surface modified with hydrophilic agents, thereby decreasing its hydrophobicity and improving its wettability. More specifically, ePTFE materials are pre-treated with plasma to activate the surface, exposed to a hydrophilic polymer and treated again with a plasma to crosslink the hydrophilic coating on the ePTFE surface.

In one embodiment of the present invention, a method of surface modifying a hydrophobic polymer substrate to increase wettability is provided comprising pre-treating a hydrophobic polymer substrate with a radio frequency (RF)-generated first plasma and a RF-generated second plasma wherein the first plasma and the second plasma are applied sequentially, coating the hydrophobic polymer substrate with a hydrophilic coating, and polymerizing the hydrophilic coating on the hydrophobic polymer substrate by exposure to a RF-generated third plasma.

In another embodiment of the present invention, the hydrophobic polymer substrate comprises an expanded polytetrafluoroethylene (ePTFE) substrate.

In another embodiment, the first RF-generated plasma comprises an inert gas plasma. In another embodiment, the inert gas plasma is an argon plasma.

In another embodiment of the present invention, the second RF-generated plasma is a reactive gas plasma. In another embodiment the reactive gas plasma is an $H_2O$ plasma.

In one embodiment of the present invention, a method of surface modifying an ePTFE substrate to increase wettability is provided comprising pre-treating the ePTFE substrate with a radio frequency (RF)-generated argon plasma and a RF-generated $H_2O$ plasma wherein the argon plasma and the $H_2O$ plasma are applied sequentially; coating the ePTFE substrate with a PEG-acrylate coating; and polymerizing the PEG-acrylate coating on the ePTFE substrate by exposure to a RF-generated argon plasma.

In yet another embodiment of the present invention, the hydrophilic coating comprises a polyethylene glycol acrylate (PEG-acrylate) polymer having the general structure $H_2C{=}CHCO(OCH_2CH_2)_nOH$, wherein n is an integer between 1 and 300. In another embodiment, n is 200.

In another embodiment of the present invention, the coating step comprises exposing the hydrophobic polymer substrate to a solution of PEG-acrylate in methanol wherein the concentration of PEG-acrylate is approximately 5% to approximately 95%. In another embodiment, the concentration of PEG-acrylate in the solution is approximately 15% to approximately 25% by weight.

In an embodiment of the present invention, the ePTFE substrate comprises an ePTFE medical device selected from the group consisting of replacement joints, tubing, vascular grafts, catheters, heart valves, ocular lenses, pacemakers, pacemaker leads and stents. In another embodiment; the ePTFE medical device comprises an vascular graft. In yet another embodiment of the present invention, the ePTFE medical device comprises an ablation catheter.

In one embodiment of the present invention, a medical device is provided comprising ePTFE wherein the medical device has a PEG-acrylate coating on at least a portion of the medical device surface, the coating deposited by exposure to at least one RF-generated plasma. In another embodiment, the medical device is selected from the group consisting of replacement joints, tubing, vascular grafts, catheters, heart valves, ocular lenses, pacemakers, pacemaker leads and stents. In yet another embodiment, the PEG-acrylate has the general structure $H_2C{=}CHCO(OCH_2CH_2)_nOH$, wherein n is an integer between 1 and 300.

DEFINITION OF TERMS

Figure 1:
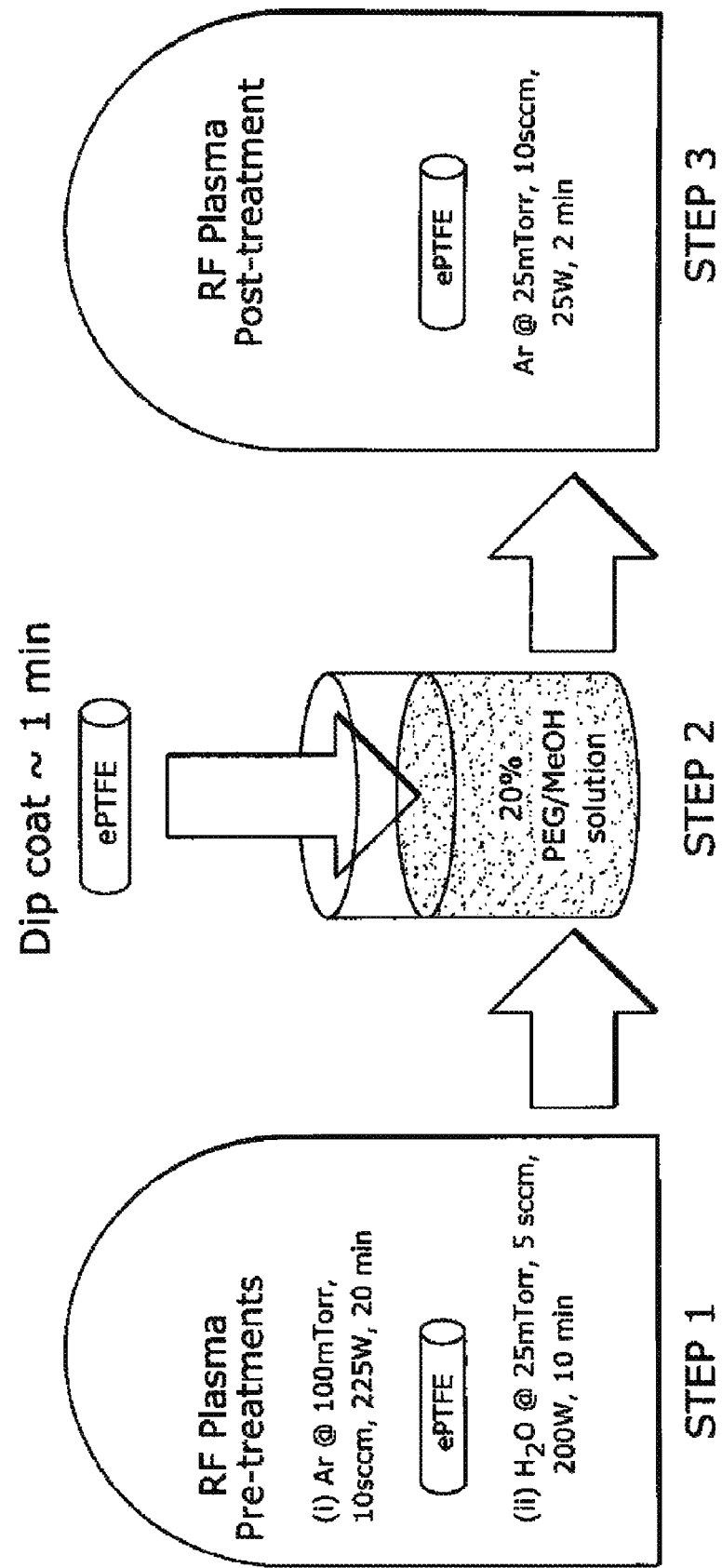
FIG. 1 graphically depicts one embodiment of the method to surface modify expanded polytetrafluoroethylene (ePTFE) according to the teachings of the present invention.

Generally, all technical terms or phrases appearing herein are used as one skilled in the art would understand to be their ordinary meaning. For the convenience of the reader, however, selected terms are more specifically defined as follows.

Biocompatible: As used herein, "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Contact Angle: As used herein, the "contact angle" is the angle at which a liquid interface meets the solid surface and is a measure of wettability. The contact angle is indicated by the symbol $\theta$. The contact angle is specific for any given system and is determined by the interaction between the solid, the liquid and vapor phases.

ePTFE: As used herein, "ePTFE" is an acronym for expanded polytetraflouroethylene. Expanded PTFE material is obtained by expanding PTFE (polytetraflouroethylene) material under controlled conditions during the manufacturing process. This process alters the physical properties of the material by creating microscopic pores in the structure of the material.

Hydrophilic: As used herein, the term "hydrophilic" refers to a material that has a high affinity for or even attracts water. The phenomenon is typically due to a predominance of polar molecules in the material, but may be caused by other factors. When referring to a solid, hydrophilic means the material has more hydrophilic matter than hydrophobic matter at least at its surface. Hydrophilic materials are readily wettable by water.

Hydrophobic: As used herein, the term "hydrophobic" refers to a material that has low or no affinity for or even repels water. The phenomenon is typically due to a predominance of non-polar molecules in the material, but may be caused by other factors. When referring to a solid, hydrophobic means the material has more hydrophobic matter than hydrophilic matter at least at its surface. Hydrophobic materials are not substantially wettable by water.

Inert Gas: As used herein, "inert gas" refers to a noble gas including the chemical elements in group 18 (old-style Group 0) of the periodic table. This chemical series contains helium, neon, argon, krypton, xenon and radon.

Plasma: As used herein, "plasma" refers to conductive assemblies of charged particles, neutrals and fields that exhibit collective effects. Further, plasmas carry electrical currents and generate magnetic fields. Moreover, plasma consists of a collection of free moving electrons and ions (atoms or molecules that have lost electrons). Energy is needed to strip electrons from atoms or molecules to make the plasma. The energy can be of various origins: thermal, electrical, or light (ultraviolet light or intense visible light from a laser). With insufficient sustaining power, plasmas recombine into neutral gas. Electrical power can be applied at different frequencies, such as, but not limited to, radiofrequencies and microwaves. Plasma can be accelerated and steered by electro-magnetic fields, which allows it to be controlled and applied.

Process pressure: As used herein, "process pressure" refers to the plasma reactor chamber pressure during plasma treatment as measured in mTorr. Generally, process pressure is less than standard atmospheric pressure so there is at least a partial vacuum present in the chamber (less than normal atmospheric pressure, 760 Torr or 14.7 psi). However, process pressures may be greater than 760 Torr.

Reactive Gas: As used herein, "reactive gas" refers to all other gases not defined as inert gas.

Substrate: As used herein, "substrate" refers to hydrophobic polymer materials, including, but not limited to, films, fabrics, membranes, tubing and medical devices.

Wet coating: As used herein, "wet coating" refers to dipping a substrate into a solution to coat the substrate.

Vacuum-assisted wet coating: As used herein, "vacuum-assisted wet coating" refers to a method of wet coating a substrate by removing all entrapped gaseous bubbles from the surfaces of the substrate with a vacuum Wettable or Wettability: As used herein, "wettable" or "wettability" refers to the ability of a solid to be covered, soaked, or dampened with water or some other liquid. Wettability is determined by thermodynamic properties, such as surface energy and surface tension. Wettability is measured by contact angle ($\theta$) formed at the three phase contact point of a drop of liquid with a solid surface (spreading or wicking into porous material). A material is determined to be completely wettable if the contact angle is 0°. A contact angle of <90° indicates partial wetting and a contact angle of >90° indicates a non-wetting surface.

DETAILED DESCRIPTION OF THE INVENTION

The present invention provides methods for modifying the hydrophobic surfaces of medical devices to render them wettable while maintaining the structural integrity and functionality of the medical device. Additionally, the medical devices of the present invention have a well adhered hydrophilic coating on luminal and exterior surfaces.

Expanded polytetrafluoroethylene (ePTFE) is a hydrophobic polymer material often used in medical devices because it is chemically stable, physically robust, biologically inert, microporous, non-toxic and biocompatible. However, a main disadvantage of ePTFE is its high hydrophobicity, therefore ePTFE medical devices and substrates are resistant to wetting.

Surface modification of ePTFE, to render it more wettable, can be accomplished by chemical methods including wet chemical modification, plasma treatment processes or a combination of the two. For example, ablation catheters are pre-wetted with alcohol before use to enhance their wettability in an aqueous environment. Methods which can yield stable, wettable ePTFE surfaces are needed.

Expanded polytetrafluoroethylene-containing medical devices that may benefit from modification to increase wettability include, but not limited to, vascular grafts, stent grafts, blood filter membranes, tubing, catheters, pacing electrodes, cell isolation devices, stents, replacement joints, pacemakers, ocular lenses and sensors. Exemplary catheters include, but are not limited to, ablation catheters. Exemplary stents include, but are not limited to, vascular stents, biliary stents and urethral stents.

The present invention provides methods for the surface modification of ePTFE surfaces using a multi-step process involving radio frequency (RF)-generated plasmas. In one embodiment of the present invention, a method is provided for surface modifying ePTFE by 1) RF plasma pre-treatment; 2) wet coating the ePTFE surface with a hydrophilic agent and 3) RF plasma post-treatment to crosslink the hydrophilic agent on the ePTFE surface (FIG. 1).

In one embodiment of the present invention, the first step comprises pre-treating the surface of a hydrophobic ePTFE substrate by exposure to at least one RF-generated plasma. Radio frequency-generated plasmas suitable for use in the first step of the method of the present invention include, but are not limited to, inert and reactive gas plasmas, or combinations thereof. Reactive gases useful for treating the surface of PTFE materials include, but are not limited to $O_2$, $N_2$, $NH_3$, $H_2S$, $H_2O$, CO, $CO_2$, $SO_2$, $SO_3$, $N_2O$ and $HN_3$. Inert gases useful in the methods of the present invention include, but are not limited to, argon, helium, neon, krypton, xenon and radon. In one embodiment of the present invention, the pre-treatment RF-generated plasma is argon plasma. In another embodiment, the pre-treatment RF-generated plasma is $H_2O$ plasma. In yet another embodiment, the pre-treatment RF-generated plasma comprises both argon plasma and $H_2O$ plasma, applied sequentially. Inert gas plasmas produce a roughened, activated surface on the ePTFE substrate. Reactive gas plasmas functionalize the ePTFE substrate. For example, and not intended as a limitation, treatment of the ePTFE polymer with $H_2O$ plasma introduces oxygen-containing carbon functional groups onto the surface of the ePTFE substrate. At this stage the ePTFE surface is prepared to accept a hydrophilic coating.

In an embodiment of the methods of the present invention, the second step comprises wet coating the ePTFE surface with a hydrophilic material. The wet coating is accomplished by methods known to persons of ordinary skill in the art including, but not limited to, dipping and vacuum-assisted wet chemical coating. Vacuum-assisted wet chemical coating is a process wherein a vacuum is applied to a chamber that contains the ePTFE substrate in a solution of the hydrophilic material. The vacuum removes the air bubbles on the porous ePTFE surfaces and forces the hydrophilic material into the pore spaces resulting in coating of the exposed surfaces. Entrapped air bubbles in the porous ePTFE substrate can inhibit performance and yield a non-uniform coating. In one embodiment of the present invention, the hydrophilic material is dissolved in an appropriate solvent, in a non-limiting example, methanol, at a concentration of between 5% and 95%. In another embodiment, the hydrophilic material is present in the solution at a concentration between 10% and 75%. In another embodiment, the hydrophilic material is present in the solution at a concentration between 12% and 50%. In another embodiment, the hydrophilic material is present in the solution at a concentration between 15% and 25%. In another embodiment, the hydrophilic material is present in the solution at a concentration of 20%.

Exemplary hydrophilic materials include, but are not limited to polysaccharides, polyols, polyethylene glycol (PEG) and PEG-acrylate polymers.

Polyethylene glycol acrylate polymers useful as hydrophilic coatings in the methods of the present invention include polymers of the general structure (Formula 1), wherein n is an integer between about 1 and about 300.

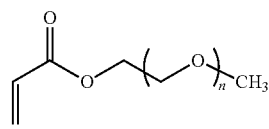

Formula 1

In one embodiment of the present invention, n is an integer between about 50 and about 275. In another embodiment, n is an integer between about 100 and about 250. In another embodiment, n is an integer between about 150 and about 225. In another embodiment, n is an integer of about 200.

In another embodiment of the present invention, the hydrophilic material used to coat the pre-treated ePTFE surface is an organic acid such as, but not limited to, acetic acid. In another embodiment of the present invention, the hydrophilic material used to coat the pre-treated ePTFE surface is a polyol such as, but not limited to, glycerol.

In another embodiment of the present invention, the third step comprises polymerizing the hydrophilic material on the ePTFE surface by exposure to RF-generated plasma. RF-generated plasmas suitable for polymerizing the hydrophilic materials include, but are not limited to, inert gas plasmas such as argon.

The RF-generated plasma pre-treatment and polymerizing processes are conducted in a closed environment at process pressures of about 10 mTorr to about 200 mTorr. In one embodiment of the present invention, process pressures are from about 10 mTorr to about 100 mTorr. In another embodiment, process pressures are from about 20 mTorr to about 50 mTorr. In another embodiment, process pressure is about 100 mTorr. In one embodiment, process pressure is about 25 mTorr.

The power for generating plasmas can vary depending upon treatment applications. The power for the generation of the RF (13.56 MHz) plasma ranges from about 15 W to about 500 W. In one embodiment of the present invention, the power ranges from about 15 W to about 500 W. In another embodiment, the power ranges from about 20 W to about 400 W. In another embodiment, the power ranges from about 30 W to about 300 W. In another embodiment, the power ranges form about 40 W to about 200 W. In another embodiment, the power ranges from 50 W to about 100 W.

Gas flows in the generation of plasma comprise various volumetric rates. Gas flow in the plasma chamber ranges from about 0.5 sccm (standard cubic centimeter per minute) to about 40 sccm. In one embodiment of the present invention, gas flow in the plasma chamber ranges from about 0.5 sccm to about 40 sccm. In another embodiment, gas flow in the plasma chamber ranges from about 0.6 sccm to about 30 sccm. In another embodiment, gas flow in the plasma chamber ranges from about 0.7 sccm to about 25 sccm. In another embodiment, gas flow in the plasma chamber ranges from about 0.8 sccm to about 20 scam In another embodiment, gas flow in the plasma chamber ranges from about 0.9 sccm to about 15 sccm. In another embodiment, gas flow in the plasma chamber ranges from about 1 sccm to about 10 sccm. In another embodiment, gas flow in the plasma chamber ranges from about 2 sccm to about 5 sccm.

Various excitation frequencies are also chosen to generate plasma. In one embodiment of the present invention, a frequency of 13.56 MHz is used to generate plasma. In another embodiment, multiples of 13.56 MHz are used to generate plasma e.g. 27.12 MHz (2×13.56 MHz). In yet another embodiment, fractions of 13.56 MHz are used to generate plasma e.g. 6.78 MHz (0.5×13.56 MHz). Frequencies in the range of microwaves are also used. In one embodiment of the present invention 2.45 GHz is used to excite the gas and generate plasma.

The degree of hydrophilicity of the surface of the surface modified ePTFE materials are measured by dynamic contact angle (DCA) analysis. For any given solid/liquid interaction there exists a range of contact angles which may be found. The value of static contact angles are found to depend on the recent history of the interaction. When the drop has recently expanded the angle is said to represent the 'advanced' contact angle. The advancing angle is defined as the angle between the surface of the water and the surface of the polymer upon initial wetting of the polymer. When the drop has recently contracted the angle is said to represent the 'receded' contact angle. These angles fall within a range with advanced angles approaching a maximum value and receded angles approaching a minimum value. The difference between the maximum (advancing) and minimum (receding) contact angle values is called the contact angle hysteresis.

The advancing angle measurement is used to determine hydrophilicity. For wettable surfaces, the advancing angle, as determined by DCA, is less than 90° while non-wettable surfaces have advancing angles greater than 90°. A complete wetting of the polymer surface is represented by an advancing angle of 0°. Water is used as the test liquid.

EXAMPLES

Example 1

Surface Modification of ePTFE with PEG-Acrylate by Dipping

An ePTFE substrate is exposed to an argon plasma with an process pressure of 100 mTorr (225 W RF power, 10 sccm Ar) for 20 minutes. Then the ePTFE substrate is exposed to $H_2O$ plasma with a process pressure of 24 mTorr (200 W RF power, 5 sccm $H_2O$) for 10 minutes. The pre-treated ePTFE substrate is then dipped in a 20% by weight solution of PEG-acrylate (n=200) in methanol for 1 minute. Then the wet-coated ePTFE substrate is exposed to argon plasma with a process pressure of 25 mTorr (25 W RF power, 10 sccm Ar) for 2 minutes. The method yields a wettable ePTFE substrate as evidenced by the advancing angle of 35.69° after treatment compared to 99.41° for the untreated ePTFE.

Analysis of PEG-acrylate coated ePTFE substrates includes dynamic contact angle with water for wettability, X-ray photoelectron spectroscopy (XPS), time of flight secondary ion mass spectroscopy (ToF-SIMS) to investigate surface chemistry and scanning electron microscopy (SEM) to evaluate the surface morphology.

The PEG-acrylate coating applied to ePTFE substrates demonstrated increased wettability and a lower advancing angle compared to the untreated ePTFE (Table 1). The PEG-acrylate coating combined with RF-plasma pre-coating and polymerizing steps resulted in ePTFE substrates with the lowest advancing angle (plasma/PEG-acrylate, Table 1). Additionally, the plasma/PEG-acrylate modified ePTFE is stable over time following storage in air and $H_2O$.

TABLE 1

Relative Wettability Measured by Dynamic Contact Angle Analysis

| ePTFE treatment | Advancing Angle (°) | Receding Angle (°) | Hysteresis (°) |
| --- | --- | --- | --- |
| Untreated | 99.41 | 77.57 | 21.84 |
| Plasma/PEG-acrylate coating | 35.69 | 26.83 | 8.86 |
| Plasma/PEG-acrylate coating stored in air for 2 weeks | 34.38 | 24.96 | 9.42 |
| Plasma/PEG-acrylate coating stored in $H_2O$ for 2 weeks | 32.21 | 26.70 | 5.51 |

Figure 2A:
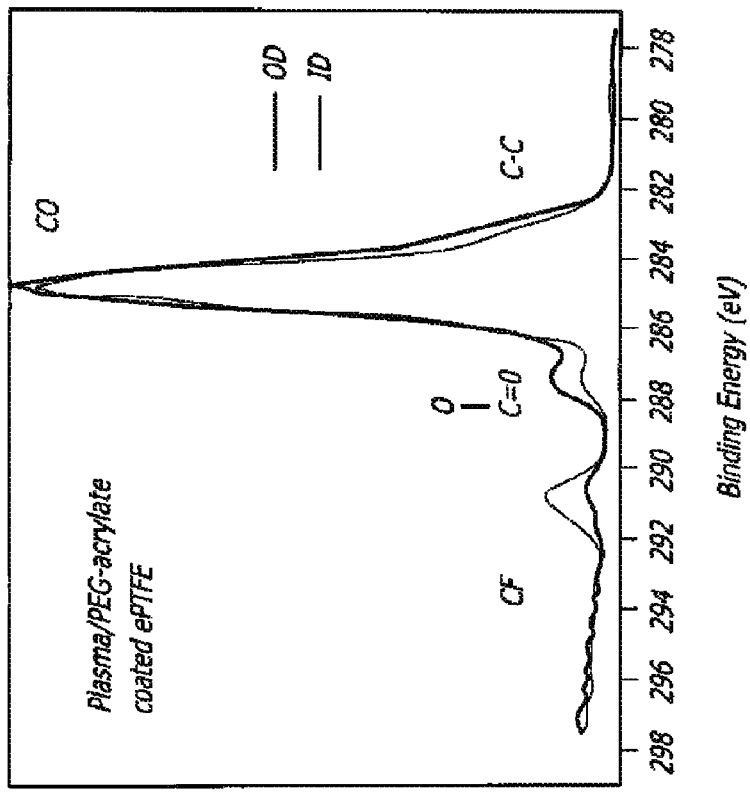
FIG. 2 depicts high resolution C1s X-ray photoelectron spectroscopy (XPS) spectral analysis of untreated ePTFE (FIG. 2A) and plasma/polyethylene glycol (PEG)-acrylate coated ePTFE (FIG. 2B) according to the teachings of the present invention. OD=outer surface; ID=inner surface.
Figure 2B:
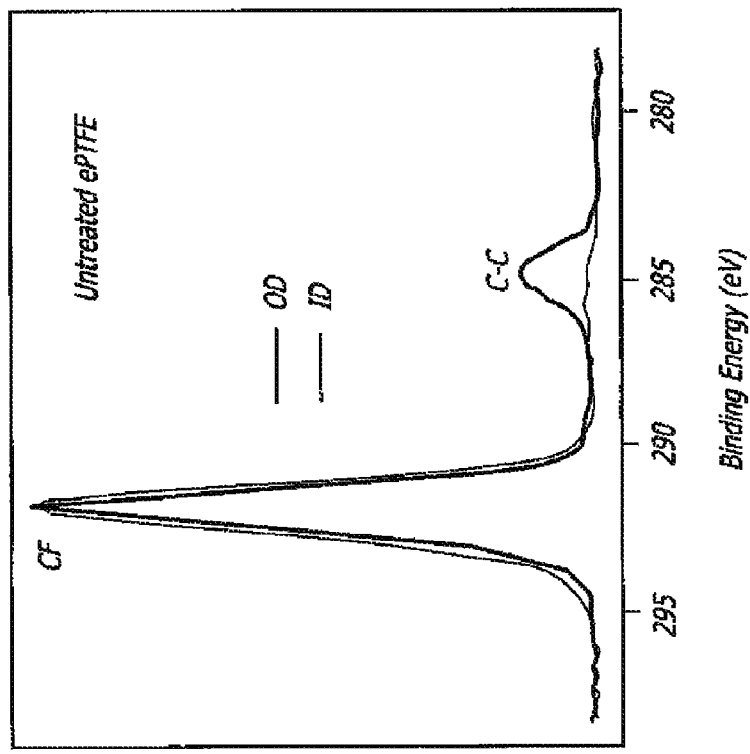

Plasma processes result in the excitation of chemical species forming ions and free radicals, therefore a variety of functional groups can form on the plasma-treated ePTFE substrate surface. XPS analysis of the inner and outer surfaces of surface modified ePTFE tubing demonstrated that the surfaces of untreated ePTFE contained mostly C and F functional groups while the PEG-acrylate treated surfaces consisted primarily of C and O functional groups (FIG. 2). Measured XPS atomic concentrations were compared with theoretical atomic concentrations for the coating based upon the chemical formula of PEG-acrylate, n=200. Table 2 below shows experimental and theoretical values. Theoretical percent atomic concentrations showed good correlation to measured values.

The XPS data demonstrate presence of a coating on the inner and outer surfaces of the ePTFE tubing following plasma treatment and that the coating retains the PEG-like structure of the monomer.

TABLE 2

Measured XPS Surface Atomic Concentrations and Calculated Bulk Atomic Concentrations

| | C | O | F |
| --- | --- | --- | --- |
| XPS-Measured Atomic Concentrations (%) | | | |
| Untreated outer surface | 33.4 | 0.5 | 66.1 |
| Untreated inner surface | 31.0 | nd | 69.0 |
| PEG-acrylate outer surface | 62.5 | 36.0 | 0.6 |
| PEG-acrylate inner surface | 63.0 | 36.0 | nd |
| Theoretical Atomic Concentrations Calculated from Chemical Structure (%) | | | |
| PEG-acrylate (n = 200) | 66.6 | 33.4 | 0 |
| PTFE $(CF_2-CF_2)_n$ (n is large) | 33.3 | 0 | 66.7 |

Figure 3A:
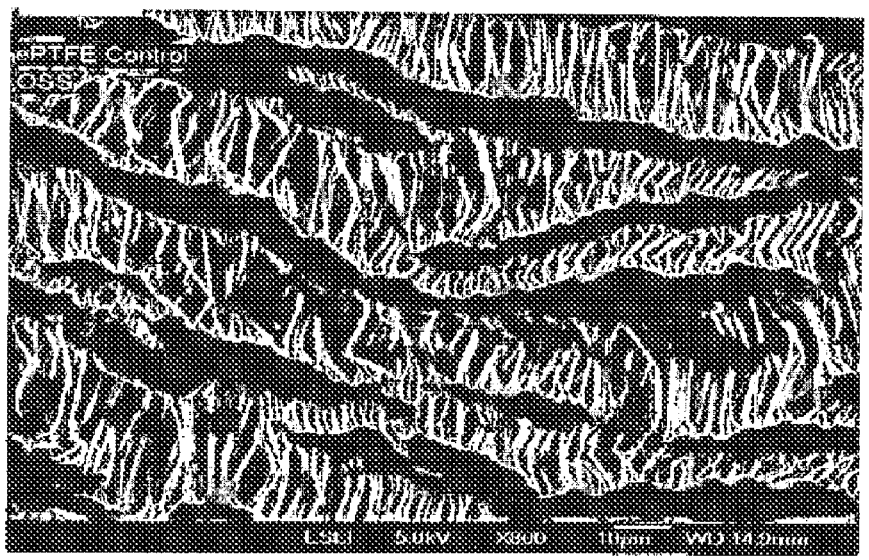
FIG. 3 depicts scanning electron microscope images of untreated ePTFE (FIG. 3A, 800×) and the outer surface of plasma treated/PEG-acrylate coated ePTFE (FIG. 3B, 1000×) according to the teachings of the present invention.
Figure 3B:
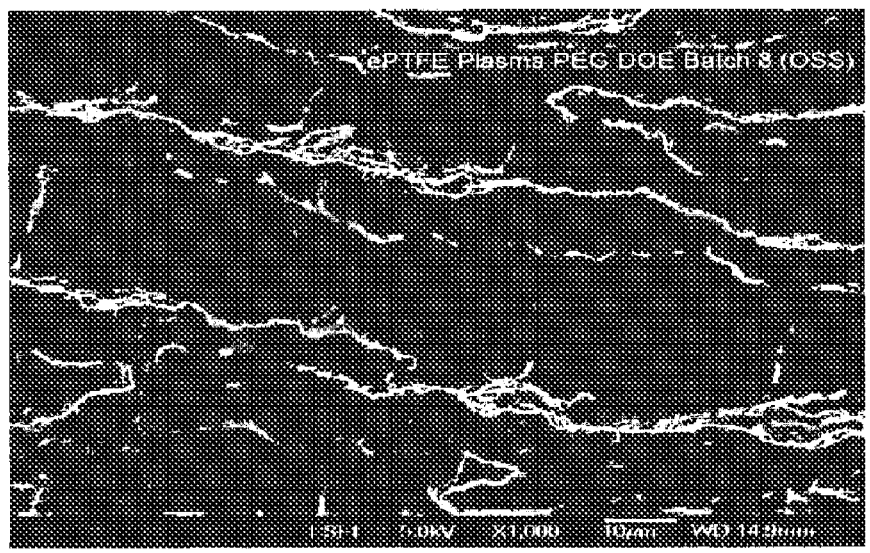

The surfaces were also analyzed by scanning electron microscopy (SEM). SEM images indicate that the plasma and PEG coating process resulted in coating on both the nodes and fibrils of the inner and outer surfaces (FIG. 3) of the ePTFE tubing.

Example 2

Surface Modification of ePTFE Tubing with PEG-Acrylate by Vacuum Assisted Wet Coating An ePTFE substrate is exposed to argon plasma with a process pressure of 100 mTorr (225 W RF power, 10 sccm Ar) for 20 minutes. Then the ePTFE substrate is exposed to $H_2O$ plasma with a process pressure of 24 mTorr (200 W RF power, 5 sccm $H_2O$) for 10 minutes. The pre-treated ePTFE substrate is removed from the plasma reactor chamber and placed in a centrifuge tube in a 20% by weight solution of PEG-acrylate (n=200) in methanol. The centrifuge tube is then placed in a beaker and enclosed in another chamber wherein a variable vacuum is drawn thereby removing air bubbles from the ePTFE pores and forcing the PEG-acrylate solution into the pores. The chamber is then brought up to atmospheric pressure and the vacuum assisted wet-coated ePTFE samples are removed and placed in the plasma reactor chamber. Then the vacuum assisted wet-coated ePTFE substrate is exposed to argon plasma with a process pressure of 25 mTorr (25 W RF power, 10 sccm Ar) for 2 minutes.

Figure 4:
FIG. 4 depicts untreated ePTFE tubing and plasma-treated ePTFE tubing coated with PEG-acrylate by the vacuum assisted technique according to the teachings of the present invention. Both samples have been stained with toluidine blue dye.

The wettability of plasma treated samples that were coated with PEG-acrylate by the vacuum assisted technique was assessed by staining with toluidine blue, a polycationic dye that stains for negative charge or polar functional groups. Since these functional groups contribute to wettability, this method was used to gauge the wettability of the porous ePTFE tubing throughout the tubing walls. Untreated and coated samples were dipped in a 1% aqueous solution of toluidine blue for 1 minute. The samples were then removed and rinsed under running water for at least 3 minutes or until the rinse water was colorless. The samples were allowed to dry before examining. A top view of stained untreated (left) and stained coated (right) samples is shown in a photograph in FIG. 4. The surface of the uncoated sample remained white after staining, suggesting that the dye did not attach to the ePTFE surface. The PEG-acrylate coated sample stained dark blue, indicating that the dye had attached to negative/polar functional groups in the PEG coating. Additionally, this blue color extended throughout the porous walls of the ePTFE tubing. This suggested that the PEG-acrylate coating had penetrated the pores and coated the pore walls and that the pore spaces within the sample were wettable.

Figure 5B:
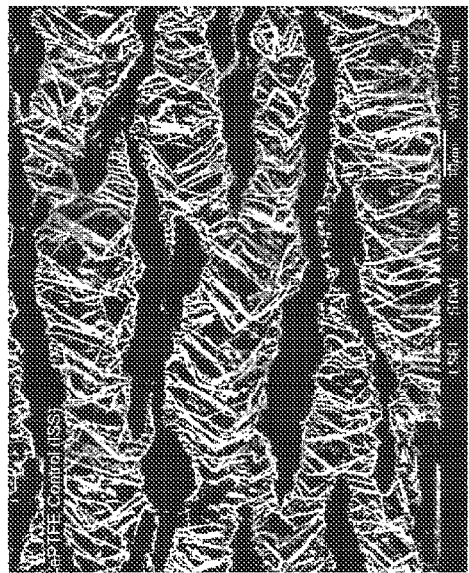
FIG. 5 depicts scanning electron microscopy images of outer (FIGS. 5A and 5C) and inner surfaces (FIGS. 5B and 5D) of plasma-treated and vacuum-grafted PEG-acrylate coated ePTFE (FIG. 5C and 5D) and uncoated ePTFE control (FIG. 5A and 5B) according to the teachings of the present invention.
Figure 5D:
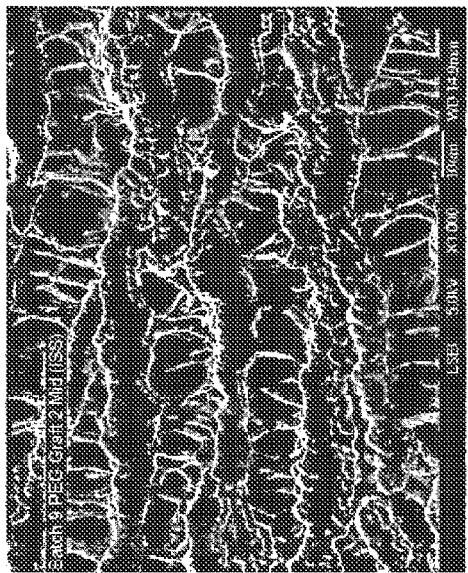
Figure 5A:
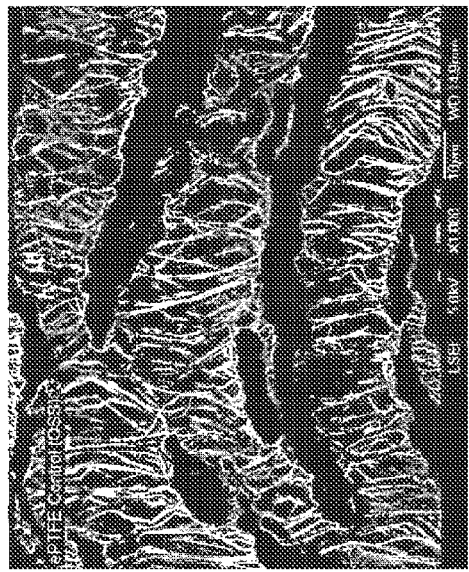
Figure 5C:
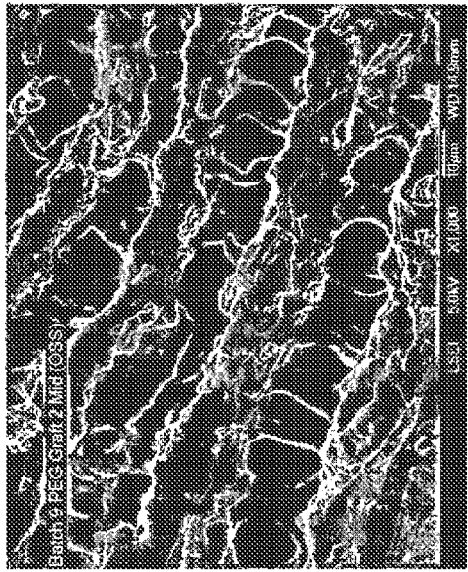

FIG. 5 depicts SEM images of outer (FIGS. 5A and 5C) and inner surfaces (FIGS. 5B and 5D) of plasma-treated and vacuum grafted PEG-acrylate coated ePTFE (FIG. 5C and 5D) and uncoated ePTFE control (FIG. 5A and 5B).

Example 3

Surface Modification of ePTFE with PEG-Acrylate by Dipping and Different Plasma Parameters Different batches of samples were made following the basic procedure of Ar plasma pretreatment, $H_2O$ plasma treatment, dipping in PEG-acrylate and Ar plasma post-treatment. Ar and $H_2O$ plasma treatment variables were varied as shown in Table 3. Additionally, for the Ar plasma treatment Ar flow was held constant at 10 sccm. For the $H_2O$ plasma treatment the pressure was held to 24 mTorr and the $H_2O$ flow rate was 5 sccm. After both plasma treatments, the pre-treated ePTFE substrate was dipped in a 20% by weight solution of PEG-acrylate (n=200) in methanol for 1 minute. Then, the wet-coated ePTFE substrate was exposed to Ar plasma with a process pressure of 25 mTorr (25 W RF power, 10 sccm Ar) for 2 minutes

TABLE 3

Plasma processing variables for Ar and $H_2O$ plasma pre-treatments.

| | Ar Pre-treatment | | | $H_2O$ Pre-Treatment | |
|---|---|---|---|---|---|
| Sample Batch | Ar Pressure (mTorr) | Ar Power (Watts) | Ar Time (min) | $H_2O$ power (Watts) | $H_2O$ Time (min) |
| 2 | 100 | 200 | 10.0 | 200 | 5.0 |
| 4 | 100 | 100 | 20.0 | 200 | 5.0 |
| 5 | 50 | 200 | 20.0 | 200 | 5.0 |
| 7 | 50 | 200 | 10.0 | 100 | 5.0 |
| 8 | 50 | 200 | 20.0 | 100 | 10.0 |

The PEG-acrylate coated ePTFE materials processed under these conditions demonstrated durable wettability. Table 4 shows the water contact angles of various batches of samples measured initially, after aging in air and aging in buffer on a shaker table. The changes in the advancing angles after aging the PEG-acrylate coated ePTFE substrate in air are minimal (0° to 10°). With additional aging in phosphate buffered saline (PBS) solution under dynamic conditions at 37° C., the advancing contact angle increases about 15° to 25°. However, the surface still retains improved wettability compared to the untreated ePTFE material (advancing contact angle=110.19°).

TABLE 4

Stability of Plasma/PEG-acrylate modified ePTFE surfaces with aging in air and in PBS solution.

| | Advancing Angle (°) | | | Receding Angle (°) | | |
|---|---|---|---|---|---|---|
| Batch | Initial | 2 mo aging in air | 2 mo aging in air + 2 wks in PBS | Initial | 2 mo aging in air | 2 mo aging in air + 2 wks in PBS |
| Untreated ePTFE | 119.02 ± 2.82 | 118.78 ± 2.23 | 110.19 ± 3.02 | 88.87 ± 2.52 | 93.69 ± 1.57 | 60.77 ± 7.44 |
| 2 | 41.17 ± 3.35 | 45.86 ± 2.76 | 62.71 ± 5.12 | 32.97 ± 1.79 | 31.45 ± 2.82 | 35.38 ± 4.34 |
| 4 | 39.33 ± 2.82 | 37.44 ± 8.32 | 63.43 ± 5.44 | 32.31 ± 2.52 | 25.07 ± 4.79 | 39.80 ± 3.06 |
| 5 | 37.40 ± 1.69 | 43.84 ± 3.94 | 57.52 ± 7.35 | 32.15 ± 2.41 | 27.71 ± 4.35 | 34.11 ± 9.30 |
| 7 | 39.64 ± 2.56 | 42.89 ± 4.77 | 66.10 ± 2.15 | 32.48 ± 1.58 | 28.79 ± 1.98 | 41.70 ± 1.52 |
| 8 | 39.30 ± 5.30 | 48.00 ± 9.43 | 59.27 ± 4.48 | 30.45 ± 1.83 | 27.89 ± 1.81 | 38.14 ± 1.88 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated by reference herein in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A medical device comprising ePTFE wherein said medical device has a PEG-acrylate coating on at least a portion of said medical device surface, wherein said PEG-acrylate has the general structure $H_2C=CHCO(OCH_2CH_2)_nOH$, and wherein n is an integer between 1 and 300.

2. The medical device of claim 1 wherein said PEG-acrylate coating is deposited by exposure to at least one RF-generated plasma.

3. The medical device of claim 1 wherein said medical device is selected from the group consisting of replacement joints, tubing, vascular grafts, catheters, heart valves, ocular lenses, pacemakers, pacemaker leads and stents.

4. The medical device of claim 2 wherein said first RF-generated plasma comprises an inert gas plasma.

5. The medical device of claim 4 wherein said inert gas plasma is an argon plasma.

6. The medical device of claim 2 wherein said RF-generated plasma is a reactive gas plasma.

7. The medical device of claim 6 wherein said reactive gas plasma is an $H_2O$ plasma.

8. The medical device of claim 3 wherein said medical device is a vascular stent.

9. The medical device of claim 3 wherein said medical device is an ablation catheter.

* * * * *